United States Patent
Vasiljevich et al.

(10) Patent No.: US 6,413,910 B1
(45) Date of Patent: *Jul. 2, 2002

(54) COMPOSITION COMPRISING CHITOSAN FOR ENHANCING RESISTANCE TO PLANT DISEASES

(75) Inventors: Novozhilov Kapiton Vasiljevich; Tjuterev Stanislav Leonidovich; Jakubchik Mikhail Sergeevich; Tarlakovskij Stanislav Aleksandrovich, all of Seut-Petersburg; Kolomiets Aleksej Filippovich, Moscow; Panarin Evgenij Fedorovich, Seut-Petersburg; Ismailov Eduard Jakovlevich; Gamza-Zade Arif Ismailovich, both of Moscow; Ismailov Vladimir Jakovlevich; Begunov Ivan Ivanovich, both of Krasnodar, all of (RU)

(73) Assignee: Iskra Industry Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/078,505

(22) Filed: May 14, 1998

(30) Foreign Application Priority Data

May 15, 1997 (RU) ............................................ 97107927

(51) Int. Cl.$^7$ .............................................. A01N 43/16
(52) U.S. Cl. ...................................................... 504/140
(58) Field of Search ............................ 504/116, 116.1, 504/140

(56) References Cited

U.S. PATENT DOCUMENTS 4,964,894 A 10/1990 Freepons ........................ 71/88
5,726,123 A * 3/1998 Heinsohn et al. ............ 504/140

FOREIGN PATENT DOCUMENTS

| EP | 0 592 964 | | 4/1994 |
| FR | 2 667 072 | | 3/1992 |
| JP | 08-12514 | * | 1/1996 |
| WO | 89/07395 | | 8/1989 |
| WO | 97/09879 | | 3/1997 |

OTHER PUBLICATIONS

Chemical Abstracts, vol. 122, No. 15, Apr. 10, 1995, Columbus, OH, US; abstract No. 188386, I.I. Begnuno et al,: "Induced resistance to fusariosis in rice plants" XP002076904, abst & Agrokhimiya, 10/94, pp. 85–87.
Database WPI, Sec. Ch, Wk 9517, Derwent Pub. Ltd, London, GB; AN 95–126070 XP002076905 & JP 07 048214 A (Mitsui Eng & Shipbuilding Co), Feb. 21, 1995, abstract.
Database WPI, Sec. CH Wk 9537, Derwent Pub. Ltd., London, GB; AN 95–281164 XP002076906 & JP 07 179843 A (Daiichi Seimo KK), Jul. 18, 1995, abstract.
Database WPI, Sec. CH, Wk 9304, Derwent Pub. Ltd., London, GB; AN 93–032634, XP002076907 & JP 04 360806 A (Yokoyama M), Dec. 14, 1992, abstract.
Database WPI, Section Ch, Wk 9335, Derwent Pub., Ltd., London, GB; AN 93–278299 XP002076908 & JP 05 194605 A (Nippon Automation KK), Aug. 3, 1993, abstract.
Database WPI, Section CH, Week, 7827, Derwent Pub. Ltd., London, GB, An 78–48578A XP002076909 & JP 53 059027 A (Nippon Soda Co), May 27, 1978, abstract.
Sigma–Aldrich Data: Product No. 22742, Synonyms: 2–Amino–2–deoxy–(1→4)–β–D–glucopyranan; Poly($1_1$4–β–D–glucopyranosamine). 2001.
Sigma–Aldrich Product Description, Chitosan—A Technologically Important Biomaterial, 1999.

* cited by examiner

Primary Examiner—S. Mark Clardy
(74) Attorney, Agent, or Firm—Foley & Lardner

(57) ABSTRACT

A composition for enhancing resistance to plant diseases comprising (1) chitosan, (2) lactic acid or succinic acid or both of the two, or the two and glutamic acid, and as the essential or optional ingredient (3) a plant activating agent such as a plant hormone, etc. It can protect plants without badly affecting the environment.

12 Claims, No Drawings

COMPOSITION COMPRISING CHITOSAN FOR ENHANCING RESISTANCE TO PLANT DISEASES

BACKGROUND OF INVENTION

1. Field of Invention

The present invention relates to the field of agriculture and more specifically to the field of combatting plant diseases and injuries by a pathogen by means of a composition comprising a natural polysaccharide, chitosan, as a main ingredient, an organic acid, and, as desired, various biologically active substances for enhancing their effect.

The present invention is much superior to any agricultural chemicals (pesticides) currently used in terms of environmental safety, can be used widely as a biological agent against diseases of, and injuries to, crops and has equal or better effects on pathogens compared to the above pesticides, for the treatment of seeds and saplings before seeding of crops, for treatment of plants during growth, and for application to the soil before dissemination (planting).

2. Related Art

Compositions comprising chitosan as a main ingredient for use in cultivation of agricultural plants as the plant growth regulator have already been known (U.S. Pat. No. 4,312,159). The known compositions include the following compounds (% by volume):

| | |
|---|---|
| chitosan | 0.1–10, mainly 2, |
| glutamic acid | 0.1–10, mainly 2, | wherein the weight ratio of chitosan to glutamic acid is 1:1.

Major disadvantages of the known compositions comprising chitosan as a main ingredient include its narrow range of functions, i.e., they function only as the plant growth regulators.

By analyzing the conventional state of the art, it was found that the activity so far known for chitosan and organic acids as well as all biologically active substances (excluding catapol, salicylic acid, and monosubstituted orthophosphite sodium) is only the growth regulating action. For catapol, only the fungicidal and the algicidal actions are so far known. Salicylic acid has been used as a fungicide and for treatment of rheumatoid diseases. For monosubstituted orthophosphite sodium, the prevention of mycosis of the seeds of the grass plants and other garden plants has been known.

SUMMARY OF INVENTION

Thus, the purpose of the present invention is to provide a novel composition which is capable of imparting to plants not only the ability of controlling the growth of the plants but resistance to a wide range of plant pathogens.

According to the first embodiment of the invention, the present invention provides a composition for enhancing resistance to plant diseases comprising the following ingredients:

(1) chitosan with a molecular weight of 800–150,000 and a degree of deacetylation of 65–97% 0.004–0.500% by weight;

(2) the following organic acids or a mixture of the organic acids (a) and (b) 0.004–0.500% by weight
  (a) lactic acid or succinic acid or both;
  (b) lactic acid or succinic acid or both, and glutamic acid or a salt thereof;

(3) one to three biologically active substances selected from the group consisting of a natural or synthetic plant hormone, a natural unsaturated fatty acid or a synthetic derivative thereof, an alkyldimethylbenzyl ammonium salt of a copolymer of N-vinyl pyrrolidone and crotonic acid, phenolic acid, and an inorganic salt; and (4) water all of the remainder, wherein the weight ratio of the ingredient (1) and the ingredient (2) is 1:1, the weight ratio of the ingredient (3) and the ingredient (1) is 0.0002–2:1, and pH is 5.6–6.0.

As the plant hormone in the above ingredient (3), there can be mentioned heteroauxin (β-indol acetate, IAA), a synthetic fluorine compound such as FF806, and the like. As the natural unsaturated fatty acid or a synthetic derivative thereof in said ingredient (3) there can be mentioned oleic acid, linoleic acid, linolenic acid, arachidonic acid or 12-oxy-cis-9-octadecenic acid methyl ether, and the like. Furthermore, as the phenolic acid in said ingredient (3), there can be mentioned, for example, salicylic acid. As the inorganic acid salt ins said ingredient (3), there can be mentioned monosodium phosphite.

According to the second embodiment of the present invention, there is provided a composition for enhancing resistance to plant diseases comprising the following ingredients:

(1) chitosan with a molecular weight of 41,600–800,000 and a degree of deacetylation of 75–90% 0.004–0.500% by weight;

(2) the following organic acids or a mixture of the organic acids (a) and (b) 0.004–0.500% by weight
  (a) lactic acid or succinic acid or both of the two;
  (b) lactic acid or succinic acid or both of the two and glutamic acid or a salt thereof;

(3) water all of the remainder, wherein the weight ratio of the ingredient (1) and the ingredient (2) is 1:1.

Preferably, the above essential ingredients are supplemented, as an optional component, with a biologically active substance (3) which is a natural or synthetic plant hormone, a natural unsaturated fatty acid or a synthetic derivative thereof as the optional ingredients. As said natural or synthetic plant hormone as the above optional ingredient, for example, there can be mentioned heteroauxin, fluoroxane(α-(4-methylaminobenzene)-β, β, β-trifluorolactic acid ethylether hydrochloride), a synthetic fluorine compound such as FF-806, and the like. Furthermore, as said natural unsaturated fatty acid or a synthetic derivative thereof as the above optional ingredient, there can be mentioned, for example, arachidonic acid, a methyl ether of 12-oxy-cis-9-octadecenic acid, and the like.

Chitosan is a natural polysaccharide, β-(1-4)-2-acetamide-2-deoxy-D-glucopyranoside, having a polymeric ring structure, and is represented by the following structural formula:

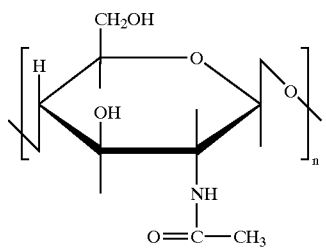

-continued

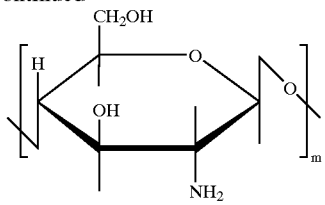

wherein, m+n is 100 mole %, n is 65–97 mole %, and the molecular weight is 300–1,000,000. In the first embodiment of the present invention, preferably the chitosan has n (degree of deacetylation) of 65–97%, and a molecular weight of 800–150,000. In the second embodiment of the present invention, the chitosan has n (degree of deacetylation) of 75–90%, and a molecular weight of 41,600–800,000.

Heteroauxin (β-indol acetate, IAA), a natural plant hormone, is a hormone having the growth promoting activity and is represented by the following chemical formula:

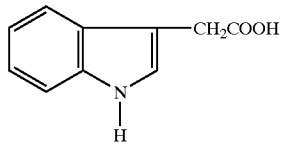

Fluoroxane, a synthetic derivative of a plant hormone, is α-(4-methylamino benzene)-β, β, β trifluorolactic acid ethyl ether hydrochloride which has the ability of controling growth (control of cell division) and is represented by the following formula:

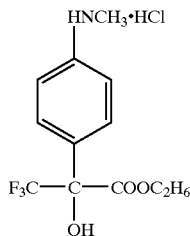

FF-806 is a synthetic fluorine compound having the ability of controling plant growth and is represented by the following formula:

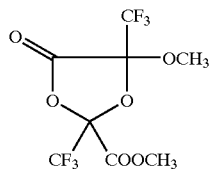

An alkyl dimethyl benzyl ammonium salt of a copolymer of N-vinyl pyrrolidone and crotonic acid is also called catapol and is represented by the following formula:

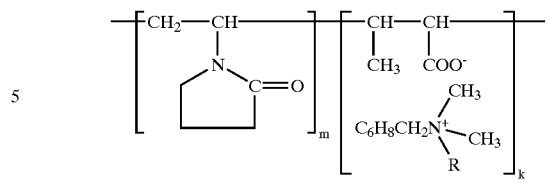

wherein, m=80–85 mole %, k=15–20 mole % R=$C_nH_{2n-1}$, n=10–18, and the molecular weight is 12,000–400,000 D.

The methyl ether of 12-oxy-cis-9-octadecenic acid has the ability of controling plant growth and is represented by the following formula:

$CH_3-(CH_2)_4-(CH=CH-CH_2)_4-CH_2CH_2-COOCH_3$.

The composition of the present invention may be obtained by dissolving chitosan in an aqueous solution of lactic acid, succinic acid, or a mixture thereof and glutamic acid with the weight ratio of chitosan and the organic acids being 1:1. The other biologically active substance additives are added to this solution as an aqueous solution. When desired (for example, in the case of IAA and FF-806), a small amount of dimethyl sulfoxide (0.05–0.1% of the final concentration of the composition) is used.

The possibility of using the composition of the present invention discovered by the inventors as an environmentally-safe biologically-active agent for plants is not obviously derived from the structure and the known property of each ingredient and the overall composition.

The effect of these compositions are inferably derived from the previously unknown ability of chitosan to enhance a nonspecific plant's resistance to harmful organisms in general as an environmentally-safe biologically-active agent. This is endorsed by Table 1. The composition of the present invention is soluble in water, has a favorable coat-forming property and permeability, has a high attachment property to the plants, is active and stable at around a neutral pH of 5.6–6.0 (when desired, pH may be adjusted by adding sodium carbonate), and has no plant toxins.

In order to demonstrate that the proposed solution is consistent with the conditions for "industrial applicability" and to permit better understanding of the nature of the invention, specific examples are presented below. However, it should be noted that the nature of the present invention is not limited to these examples.

The activity of the composition of the present invention as an environmentally-safe plant protecting agent active against a wide range of pathogens at various stages of plant growth was discovered for the first time by the inventor of the present invention, and the activity cannot be obviously derived from the structures and the known properties of these compositions and the ingredients thereof as a whole.

As far as can be inferred, the effect of the composition of the present invention is based on the so far unknown ability of chitosan that, when the environmentally-safe biologically active chitosan is combined with other ingredients of the composition, acts as a plant activating agent which is resistant to diseases caused by a series of harmful organisms, due to differences in the material metabolism between the pathogen and the plant.

The substances having the above-mentioned activity are limited to particular combinations of chitosan with strictly specified organic acids and several other compounds. This is related to the fact that the present composition induces disease resistance in plants by the following two methods:

By the increase in the oxidation potential of the cell. The oxidation potential is enhanced by the natural fatty acids having unsaturated (double) bonds (oleic acid, linoleic acid, linolenic acid, and arachidonic acid) or the unsaturated analogues thereof (local disease-resistance).

By the activation of the protective genes of plants. This activation is derived from the presence of a specific natural or synthetic hormone (for example, IAA, and FF-806), a phenolic acid (for example, salicylic acid) and an inorganic acid (for example, $NaH_2PO_4$) in the ingredients of the composition, which causes systemic disease resistance in the plant tissues.

Therefore, by various biologically active substances and the compositions thereof, the same technical results (the enhancement of disease resistance in plants) can be obtained by the same method.

The composition of the present invention is soluble in water, has a favorable coat-forming property and permeability, has a high adherent property to the plants, is active and stable at around a neutral pH of 5.6–6.0 (when desired, pH may be adjusted by adding sodium carbonate), and has no toxicity to plants in the range of concentrations commonly used.

By utilizing the present invention, even a marked reduction in the concentration of a biologically active substance (heteroauxin 2 g, fluoroxane 0.2 g, FF-800 5 g, catapol 25–1.0 kg) can provide remarkably good protective results against diseases and injuries to crops, which leads to the improvement of ecologically-acceptable labor conditions and the prevention of contamination of the environment and crops by residual agricultural chemicals.

EXAMPLES

In order to demonstrate that the solution proposed herein is consistent with the requirements of "industrial applicability" and to permit more accurate understanding of the spirit of the present invention, specific examples are presented hereinbelow. It should be noted, however, that the spirit of the present invention is not limited to these examples.

Examples 1–9

Examples 1–9 demonstrate the characteristics of the function of each biologically active substance in the development of the effects of the composition of the present invention having an aqueous solution of chitosan as the main ingredient, when seeds of barley are treated and when the seeds and the barley during growth are totally treated in order to combat a series of diseases. The cultivation of spring barley (variety Abava) was conducted at the experimental farm of a limited company "Tversky Seeds" (Tver region) under the same field test condition in background of the natural infection factors. The soil of the experimental farm is a light loam podzol sod and is drained by a conduit. The size of one compartment of the experimental section is 30 square meters and the experiment was conducted three times. The analysis of the plant pathological evaluation and the yield structure was conducted based on a commonly used method ("Methodological Instructions on the National Testing on Pesticides, Antibiotics and Disinfectants of Crop Seeds," Moscow, 1985, page 130).

The data in Examples 1–9 are shown in Table 1 and 2, which are comparable with each other. Table 1 (Examples 1–5) show the data obtained when the composition having the composition of the present invention was used for treatment of the seeds before seeding. Table 2 (Examples 1, 6–9) show the result of the total treatment including not only the seed treatment before seeding but also the two treatments during the tillering and earring periods of the growing barley.

The data on the pathogenicity and productivity of the control plants (the barley which was not treated) are shown in Example 1 of Table 1 and 2. For comparison of the composition of the present invention, the widely used pesticide Baitan U (Bayer, Germany) 2 kg/t ("A list of chemicals, biological pesticides, growth regulators and pheromones permitted to be used in the field of agriculture during 1992–1996 for combatting and exterminating pests, diseases, and weeds," Cosmo (ear) publishing company, Moscow, 1994) was used for the treatment of the seeds (Examples 5 and 9), and BT (biological pesticide) dusting powder on the leaves (Bayer, Germany) 1 liter/ha (8) was used for the treatment of plants during growth (Example 9). Red stele in Examples 1–9 is represented by the pathogens *Helminthosporium sativum* Pamm. King et Bakke and Fusarium Sp., and the blotches of the leaves by the leaf spot-causing organisms are represented by the pathogens *Helminthosporium sativum* Pamm. King et Bakke and Drechslera teres Ito.

For treatment of the seeds, the following compositions were used in terms of % by weight:

Example 2: chitosan—0.3, succinic acid—0.20, glutamic acid—0.1, water—less than 100;

Example 3: chitosan—0.3, succinic acid—0.20, glutamic acid—0.1, heteroauxin—0.006 (6), water—less than 100;

Example 4: chitosan—0.3, succinic acid—0.20, glutamic acid—0.1, FF-806—0.016 (U.S. Pat. No. 4,312,159), water—less than 100;

The amount used of the composition for seed treatment—30 liters/t.

All the data on Examples 1–5 are shown in Table 1.

TABLE 1

| | Root blight extension (%) at stages | | | Decreasing of disease severity (%) to control at stages | | |
| --- | --- | --- | --- | --- | --- | --- |
| Example | Tillering | Milky-wax ripeness | Lipening | Tillering | Milky-wax ripeness | Lipening |
| 1 | 6.2 | 25.0 | 38.3 | — | — | — |
| 2 | 4.1 | 19.6 | 34.1 | 33.9 | 21.6 | 11.0 |
| 3 | 2.7 | 18.1 | 29.2 | 56.4 | 27.6 | 23.8 |
| 4 | 1.9 | 17.1 | 27.9 | 69.3 | 31.6 | 27.1 |
| 5 | 1.0 | 14.2 | 30.5 | 83.9 | 43.2 | 20.4 |

TABLE 1-continued

| | Helminthosporiom leaf blight extension (%) at stages | | | Decreasing of disease severity (%) to control at stages | | |
|---|---|---|---|---|---|---|
| Example | Tillering | Earring period | Milky-wax ripeness | Tillering | Earring period | Milky-wax ripeness |
| 1 | 8.5 | 25.0 | 72.5 | — | — | — |
| 2 | Single | 18.0 | 72.0 | 88.2 | 28.0 | — |
| 3 | Single | 16.9 | 75.0 | 88.2 | 32.4 | — |
| 4 | Single | 16.0 | 71.2 | 88.2 | 36.0 | — |
| 5 | Single | 13.2 | 65.0 | 88.2 | 47.2 | 10.3 |

| | Yield structure | | | | | | |
|---|---|---|---|---|---|---|---|
| Example | Number of stems with ears (Stems/sq. meter) | Height of plant (cm) | Length of ear (cm) | Number of grains in ear (pieces) | Weight of 1,000 grains (g) | Biological yield (t/ha) | To control (%) |
| 1 | 472.3 | 84.2 | 7.1 | 18.0 | 38.1 | 3.24 | 100 |
| 2 | 478.3 | 85.1 | 7.2 | 18.4 | 40.0 | 3.52 | 108.6 |
| 3 | 486.0 | 87.4 | 7.3 | 18.0 | 41.0 | 3.59 | 110.8 |
| 4 | 485.3 | 87.9 | 7.3 | 18.0 | 41.0 | 3.59 | 110.5 |
| 5 | 490.0 | 85.0 | 7.1 | 18.1 | 39.0 | 3.46 | 106.8 |

The compositions for treatment of the seeds in Examples 6, 7, and 8 are the same as those in Examples 2, 3, and 4.

For spraying to the plants during the tillering and the earring periods, the compositions with following composition were used in terms of % by weight:

Example 6: chitosan—0.05, succinic acid—0.03, glutamic acid—0.02, water—less than 100;

Example 7: chitosan—0.05, succinic acid—0.03, glutamic acid—0.02, heteroauxin—0.05, water—less than 100;

Example 8: chitosan—0.05, succinic acid—0.03, glutamic acid—0.02, FF-806—0.05, water—less than 100;

The amount used of the composition for seed treatment—200 liters/ha.

All the data on Example 1, and 6–9 are shown in Table 2.

TABLE 2

| | Root blight extension (%) at stages | | | Decreasing of disease severity (%) to control at stages | | |
|---|---|---|---|---|---|---|
| Example | Tillering | Milky-wax ripeness | Lipening | Tillering | Milky-wax ripeness | Lipening |
| 1 | 6.2 | 25.0 | 38.3 | — | — | — |
| 6 | 3.7 | 18.9 | 30.2 | 40.3 | 24.4 | 21.1 |
| 7 | 2.1 | 16.0 | 27.5 | 66.1 | 36.0 | 28.2 |
| 8 | 2.0 | 16.1 | 26.7 | 67.7 | 35.6 | 30.3 |
| 9 | 1.3 | 13.8 | 28.4 | 79.0 | 44.6 | 25.8 |

| | Helminthosporiom leaf blight extension (%) at stages | | | Decreasing of disease severity (%) to control at stages | | |
|---|---|---|---|---|---|---|
| Example | Tillering | Earring period | Milky-wax ripeness | Tillering | Earring period | Milky-wax ripeness |
| 1 | 8.5 | 25.0 | 72.5 | — | — | — |
| 6 | Single | 18.2 | 70.0 | 88.2 | 47.2 | — |
| 7 | Single | 11.0 | 72.3 | 88.2 | 56.4 | — |
| 8 | Single | 12.0 | 72.8 | 88.2 | 51.6 | — |
| 9 | Single | 10.0 | 65.5 | 88.2 | 60.0 | 9.6 |

| | Yield structure | | | | | | |
|---|---|---|---|---|---|---|---|
| Example | Number of stems with ears (Stems/sq. meter) | Height of plant (cm) | Length of ear (cm) | No. of seeds/ ear (pieces) | Weight of 1,000 grains (g) | Biological yield (t/ha) | To control (%) |
| 1 | 472.3 | 84.2 | 7.1 | 18.0 | 38.1 | 3.24 | 100 |
| 6 | 481.0 | 87.7 | 7.3 | 18.1 | 41.1 | 3.58 | 110.5 |
| 7 | 490.0 | 89.2 | 7.3 | 17.9 | 41.1 | 3.60 | 111.1 |

TABLE 2-continued

| 8 | 490.0 | 89.0 | 7.3 | 17.9 | 41.1 | 3.60 | 111.1 |
| 9 | 480.6 | 86.8 | 7.1 | 18.0 | 40.1 | 3.47 | 107.1 |

Note: In Examples 6–8, thitosan having the molecular weight of 150000 D and the deacetylation degree of 85% were used.

Examples 10–14

Examples 10–14 demonstrate the effectiveness of the effects of the compositions containing chitosan, lactic acid and the additional ingredients (12-oxy-cis-9-octadecenic acid methyl ether). The effectiveness was studied using as the example the combatting of potato's late blight pathogen (*Phytophthora infestans* [Mont.] de Bary). The examples were conducted under the condition which permits comparison with one another, that is, using the method in which the slice of the potato (Gatchinsky sp.) was artificially infected (inoculated) with the suspension of the conical of the organism (200,000 conidium per ml). The state of the disease was evaluated based on the five-stage scoring for 5 days after inoculation. All the data are shown in Table 3.

stele pathogen *Helminthosporium sativum* Pamm. King et Bakke. The Examples were conducted in the background of artificial infection of wheat (Leningradka sp.) with *H. sativum*. The treatment of the seeds of wheat was conducted by the method of immersing them in the composition solution for 18 hours. Then, inoculation to the germinated seeds was conducted by the method of immersing in the suspension of *H. sativum* spores (80,000 spores per ml) for 24 hours. The wheat was grown under artificial illumination by the roll cultivation method. The pH of the composition was 6.0. The state of the disease was evaluated based on the 4-stage scoring for the wheat on day 12 after germination. All the data are shown in Table 4.

TABLE 3

| | Composition contents (% by weight)* | | | Grade of disease | Disease severity | |
|---|---|---|---|---|---|---|
| Example | Chitosan | Lactic acid | Methyl ester of decenoic acid | extension (5 stages) | To control (%) | Disease suppression (%) |
| 10 | Control (water treatment) | | | 4.4 | 10.0 | — |
| 11 | 0.1 | 0.1 | — | 0.5 | 11.4 | 88.6 |
| 12 | 0.5 | 0.5 | — | 0 | 0 | 100 |
| 13 | 0.1 | 0.1 | 0.01 | 0.14 | 3.2 | 96.8 |
| 14 | — | — | — | 1.8 | 40.9 | 59.1 |

*Remaining water to 100%
Note: In the examples, chitosan having a molecular weight of 41600 D and a degree of deacetylation of 75% was used.

Examples 15–31

Examples 15–31 demonstrate the high biological effectiveness of the composition of the present invention when the seeds of wheat were treated for to combat the crop red

TABLE 4

| | Composition contents (% by weight)* | | | Chitosan dosage | Disease severity | | |
|---|---|---|---|---|---|---|---|
| Example | Chitosan | Succinic acid | Catapol | (kg/1000 seeds) | Grade of disease extension (4 stages) | To control (%) | Biol. yield (%) |
| 15 | Comparative example — water | | | — | 2.13 ± 0.13 | 100 | 0 |
| 16 | 0.005 | 0.005 | — | 0.025 | 0.85 ± 0.07 | 39.91 | 60.09 |
| 17 | 0.010 | 0.010 | — | 0.050 | 0.87 ± 0.06 | 40.85 | 59.15 |
| 18 | 0.025 | 0.025 | — | 0.125 | 1.00 ± 0.05 | 46.95 | 53.05 |
| 19 | 0.050 | 0.050 | — | 0.250 | 1.06 ± 0.06 | 49.77 | 50.23 |
| 20 | 0.100 | 0.100 | — | 0.500 | 1.09 ± 0.06 | 51.17 | 48.83 |
| 21 | 0.005 | 0.005 | 0.005 | 0.025 | 0.89 ± 0.35 | 41.78 | 58.22 |
| 22 | 0.010 | 0.010 | 0.010 | 0.050 | 0.65 ± 0.18 | 30.52 | 69.48 |
| 23 | 0.025 | 0.025 | 0.025 | 0.125 | 0.58 ± 0.12 | 27.23 | 72.77 |
| 24 | 0.050 | 0.050 | 0.050 | 0.250 | 0.70 ± 0.16 | 32.86 | 67.14 |
| 25 | 0.100 | 0.100 | 0.100 | 0.500 | 0.38 ± 0.10 | 17.84 | 82.16 |
| 26 | 0.005 | 0.005 | 0.010 | 0.025 | 0.46 ± 0.11 | 21.60 | 78.40 |
| 27 | 0.010 | 0.010 | 0.020 | 0.050 | 0.57 ± 0.19 | 26.76 | 73.24 |
| 28 | 0.025 | 0.025 | 0.050 | 0.125 | 0.51 ± 0.11 | 23.94 | 76.06 |
| 29 | 0.050 | 0.050 | 0.100 | 0.250 | 0.40 ± 0.10 | 18.78 | 81.22 |

TABLE 4-continued

|  | Composition contents (% by weight)* | | | Chitosan dosage | Disease severity | | Biol. yield |
|  | | | | | Grade of disease extension | To control | |
| Example | Chitosan | Succinic acid | Catapol | (kg/1000 seeds) | (4 stages) | (%) | (%) |
| --- | --- | --- | --- | --- | --- | --- | --- |
| 30 | 0.100 | 0.100 | 0.200 | 0.500 | 0.21 ± 0.08 | 9.86 | 90.14 |
| 31 | | | | — | 0.33 ± 0.09 | 15.49 | 84.51 |

*Water — Less than 100
Note: In the examples, chitosan having a molecular weight of 80000 D and the degree of deacetylation of 75% was used.

Examples 32–36

Examples 32–36 demonstrate the effectiveness of the effect of the composition in the protection of young tomato buds (Volgogradsky 5/95 sp.) against the bacterial red stele pathogen (*Erwinia Carotovora* (Jones)-Holl.). The examples were conducted under the condition which permits comparison with one another. The tomato seeds were immersed in the solution of the composition of the present invention containing 0.5% chitosan (1 g of the seeds per ml of the solution) for 4 hours. Then, after 18–24 hours, the seeds were cultivated in the Petri dish by creating the infection background by the method of similarly immersing them in the liquid medium of the bacteria (one million—three million bacteria per ml). The degree of diseases of and injuries to the plants were evaluated based on staging of the young buds on day 10 by the standard method. All the data are shown in Table 5. For the sake of comparison, the 80% suspension of the seed disinfectant TMTD (tetramethylthiuram disulfide) was used which has been proposed for this purpose.

composition having the composition of the present invention in the protection of wheat against the powdery mildew pathogen (*Erysiphe graminis* DC. f. sp. tritici March). The examples were conducted under the condition which permits comparison with one another. The composition comprising chitosan at a concentration of 0.1% by weight was sprayed onto the wheat (Kharkovskaya, 46 species) at the stage of 2 leaves and after 24 hours the conidium of the pathogen are inoculated. The state of powdery mildew was evaluated on day 7 and 11 after the infection. For the sake of comparison, the bactericide VTN at a concentration of 0.0001% by weight was used in Example 42 ("The 50th Germany Meeting of Infectious Disease Control, Munster, Sep. 23–26, 1996)," "Federation Meeting of Agricultural and Forestry Biology," Berlin-Dahlem Publishing Co., No. 321, Berlin, 1996, page 259). All the data are shown in Table 6.

TABLE 5

|  | Composition contents (% by weight)* | | | Disease severity | Degree of disease |
| Example | Chitosan | Succinic acid | Catapol | (%) | vs. Com. Ex. (%) |
| --- | --- | --- | --- | --- | --- |
| 32 | Comparative example — water | | | 42.2 ± 0.8 | — |
| 33 | 0.5 | 0.5 | — | 27.0 ± 2.9 | 36.0 |
| 34 | 0.5 | 0.5 | 0.5 | 17.3 ± 0.8 | 59.0 |
| 35 | 0.5 | 0.5 | 1.0 | 14.3 ± 4.2 | 66.1 |
| 36 | A 80% suspension of seed disinfectant tetramethyl thiuram | | | 19.3 ± 2.1 | 54.3 |

*Remaining — water to 100%

Examples 37–42

Examples 37–42 demonstrate the effectiveness of the

TABLE 6

|  | Composition contents (% by weight) | | | | Disease severity (%) | | Grade of disease extension (%) | |
| Example | Chitosan | Lactic acid | Salicylic acid | NaH₂PO₃ | After 7 days | After 11 days | After 7 days | After 11 days |
| --- | --- | --- | --- | --- | --- | --- | --- | --- |
| 37 | Comparative example — water | | | | 34.6 ± 1.5 | 59.5 ± 2.4 | — | — |
| 38 | 0.1 | 0.1 | 0.05 | — | 6.4 ± 2.0 | 17.6 ± 7.3 | 81.5 | 70.4 |
| 39 | 0.1 | 0.1 | 0.05 | 0.002 | 3.2 ± 2.1 | 6.0 ± 3.2 | 90.8 | 98.9 |
| 40 | 0.1 | 0.1 | 0.05 | 0.1 | 3.9 ± 0.3 | 16.2 ± 7.6 | 88.7 | 72.7 |
| 41 | 0.1 | 0.1 | 0.05 | 0.5 | 16.7 ± 1.9 | 37.4 ± 6.1 | 51.7 | 37.2 |
| 42 | Disinfectant VTN having A.I. at a concentration of 0.0001% by weight | | | | 7.0 ± 4.3 | 28.5 ± 6.5 | 79.8 | 52.0 |

Note: In the experiments, chitosan having a molecular weight of 10000 D and a degree of deacetylation of 80% was used.

The composition of the composition for seed treatment is as follows in terms of % by weight.

Chitosan—0.3, succinic acid—0.2, glutamic acid—0.06, heteroauxin—0.006, salicylic acid—0.06, catapol—0.3, water—less than 100.

The amount used of the composition—30 liters/t.

The composition of the composition for spraying is as follows in terms of % by weight:

Chitosan—0.05, succinic acid—0.05, salicylic acid—0.05, water—less than 100.

The amount used of the composition—200 liters/ha.

Examples 43–46

The data of Examples 43–46 are presented in Table 7 and they can be compared with one another.

of each of the experimental compartment and the control compartment was 0.1 ha and the experiment was conducted three times. The compartments are systematically positioned in a line. The seeds were treated with the composition of the present invention (the amount of chitosan, 0.1 kg/t) and Baitan U (the amount, 2 kg/t) using the PSSh-5 type disinfection machine. Spraying to the plants was conducted using the OP-2000 type tractor sprayer (the amount of chitosan in the composition of the present invention is 0.1 kg/ha, the amount of tilt ("A list of chemicals, biological pesticides, growth regulators and pheromones permitted to be used in the field of agriculture during 1992–1996 for combatting and exterminating pests, diseases, and weeds," Cosmo (ear) publishing company, Moscow, 1994) 0.5 kg/ha).

Seeding was conducted using the SZ-3,6 seeding machine. The analysis of the plant pathological evaluation

TABLE 7

| Ex. | Root blight extension (%) at stages ||| Decreasing of disease severity (%) to control at stages ||| Extension of Helminthosporium leaf blight (%) at stages ||| Decreasing of disease severity (%) to control at stages |||
|---|---|---|---|---|---|---|---|---|---|---|---|---|
|  | Tillering | Earring period | Milky-wax ripeness | Tillering | Earring period | Milky-wax ripeness | Tillering | Earring period | Milky-wax ripeness | Tilling | Earring period | Milky-wax ripeness |
| 43 | 6.8 | 19.3 | 29.7 | — | — | — | Single* | 12.3 | 14.8 | — | — | — |
| 44 | 2.1 | 8.2 | 20.0 | 69.1 | 57.5 | 32.7 | 0 | 7.4 | 15.0 | — | 39.8 | 0 |
| 45 | 6.0 | 15.4 | 31.0 | — | — | — | Single | 11.1 | 14.0 | — | — | — |
| 46 | 0.2 | 6.0 | 18.0 | 96.7 | 61.0 | 41.9 | 0 | 4.2 | 13.0 | — | 62.2 | 2.1 |

| Ex. | Richsporium extension (%) at stages ||| Decreasing of disease severity (%) to control at stages ||| Septorin extension at stage of milky-wax ripeness (%) || Decreasing of disease severity (%) to control at stages ||
|---|---|---|---|---|---|---|---|---|---|---|
|  | Tillering | Earring period | Milky-wax ripeness | Tillering | Earring period | Milky-wax ripeness | Leaf | Ear | Leaf | Ear |
| 43 | Single | Single | 7.9 | — | — | — | 17.0 | 5.2 |  |  |
| 44 | 0 | Single | 4.6 | — | — | 41.8 | 8.2 | 3.9 | 51.8 | 25.0 |
| 45 | Single | Single | 8.0 | — | — | — | 16.2 | 5.3 |  |  |
| 46 | 0 | Single | 3.1 | — | — | 61.3 | 6.0 | 2.8 | 63.0 | 47.2 |

| | Yield structure |||||||||||
|---|---|---|---|---|---|---|---|---|---|---|---|
|  | No. of stems with ears || Efficiency of ear formation || Number of grains in ear || Weight of 1000 grains || Biological yield ||
| Ex. | (pcs./m2) | To control (%) | Coefficiency | To control (%) | (pcs.) | To control (%) | (g) | To control (%) | (t/ha) | To control (%) |
| 43 | 634 | 100 | 1.53 | 100 | 21 | 100 | 48.4 | 100 | 6.44 | 100 |
| 44 | 642 | 101.3 | 1.74 | 113.7 | 23 | 109.5 | 49.0 | 101.2 | 7.23 | 112.3 |
| 45 | 707 | 100 | 1.67 | 100 | 20 | 100 | 47.8 | 100 | 6.75 | 100 |
| 46 | 698 | 98.7 | 1.88 | 112.6 | 22 | 110.0 | 49.5 | 103.6 | 7.60 | 112.6 |

*Single = single spot
Note: In the experiments, chitosan having a molecular weight of 105000 D and a degree of deacetylation of 90% was used.

Examples 43–46 demonstrate the effectiveness, against a series of diseases of wheat, of the composition of the present invention containing chitosan, IAA, catapol, and salicylic acid. The experiment on the composition of the present invention was conducted using spring barley at the permanent experimental farm at VNIIMZ (All Union Institute for Mechanization of Crop Cultivation) (Tver oblast). The sod of the experimental farm is the humus podzol soil and is drained by a conduit. The composition of the present invention was tested under the condition of the biological cultivation system. As the reference sample, the chemical combatting system using the pesticide Baitan U, tilt was used (Example 46).

In each cultivation system a control example using no combatting agent was set up (Examples 43 and 45). The size was conducted based on the commonly used method ("Methodological Instructions on the National Testing on Pesticides, Antibiotics and Disinfectants for Crop Seeds," Moscow, 1985, page 130) before the regular spraying of the chemical during the tillering period, the earring period, and the maturity period. The analysis of the yield structure and the evaluation of the biological yield were conducted for the evaluation area of 1 m² unit.

The natural infection background in the control examples (Examples 43 and 45) in which no combatting agent was used was practically the same in any cultivation system, and tended to increase throughout the growth processes of barley. As a whole, the natural infection background was sufficient to evaluate the biological effectiveness of the composition of the present invention. Red stele in Examples 43–46 are represented by the pathogens *Helminthosporium sativum* Pamm. King et Bakke and *Fusarium* Sp., and the blotches of the leaves by the leaf spot-causing organisms are represented by the pathogens *Helminthosporium sativum* Pamm. King et Bakke (dark brown blotches) and Drechslera teres Ito (meshed blotches), and Drechslera graminea Ito (striped blotches). The pathogen of *Rhynchosporios* is *Rhynchosporium graminicola* Heins, and that of Septorios is *Septoria nodurum* Berk.

Examples 47–49

Examples 47–49 are shown in Table 9. The table shows that these compositions, even at high concentrations (chitosan content, 0.1–0.2% by weight), do not directly inhibit the pathogen of grain's red stele (*Helminthosporium sativum* Pamm. King et Bakke). The pesticidal effect was evaluated in vitro by adding the composition to the agar-containing Petri dish till it reaches the corresponding final concentration. To the Petri dish was inoculated the mycelium of a pure organism. On day 4, the diameter of the colony was measured and the result was expressed in terms of % relative to the result of the blank test. The number of repetitions of the experiment was 4. The data in Table 8 demonstrate that the preventive function of the composition lies in the enhancement of the plant's resistance against diseases.

the compositions with different concentrations have on the treatment of the seeds against the injuries by the pathogen of grain's red stele, *H. sativum,* and also the enhancement of the effect obtained when catapol was added to the composition.

The experiment was conducted with wheat (Leningradka sp.) using the artificial infection background of *H. sativum.* The seeds of wheat were treated by immersing them into the solution of the composition for 18 hours. Among them, the germinated seeds were inoculated by immersing them into the suspension of the *H. sativum* spores (80,000 spores/ml) overnight. The wheat was grown under artificial illumination by the coil-form cultivation method. The pH of the composition was 6.0. The state of the disease was recorded for the wheat on day 12 based on the 4-stage scoring. All the data are shown in Table 9.

TABLE 8

| Ex. | Molecular weight of chitosan (× 1000) | Degree of deacetylation (%) | Chitosan Concentration (%) | Composition contents (Weight ratio) | | | Diameter of fungal colony vs. Com. Ex. (%) |
|---|---|---|---|---|---|---|---|
| | | | | Chitosan | Succinic acid | Glutamic acid | |
| 47 | 150 | 85 | 0.05 | 5 | 3 | 2 | 106.5 ± 1.6 |
| 48 | 150 | 85 | 0.10 | 5 | 3 | 2 | 93.0 ± 8.3 |
| 49 | 150 | 85 | 0.20 | 5 | 3 | 2 | 84.0 ± 1.7 |

Examples 50–66

Examples 50–66 are derived from the experiments under the conditions comparable with one another. All the data are shown in Table 10, which shows the evaluation of the effect

TABLE 9

| Ex. | Composition contents (Weight ratio) | | | Chitosan Concentration (%) | Amount of chitosan per ton of seeds (kg) | Disease development | | Biological effect (%) |
|---|---|---|---|---|---|---|---|---|
| | Chitosan | Succinic acid | Glutamic acid | | | In grade (4 stages) | To control (%) | |
| 50 | Comparative Example — Water | | | — | — | 2.13 ± 0.13 | 100 | 0 |
| 51 | 1 | 1 | — | 0.005 | 0.025 | 0.85 ± 0.07 | 39.91 | 60.09 |
| 52 | 1 | 1 | — | 0.010 | 0.050 | 0.87 ± 0.06 | 40.85 | 59.15 |
| 53 | 1 | 1 | — | 0.025 | 0.125 | 1.00 ± 0.05 | 46.95 | 53.05 |
| 54 | 1 | 1 | — | 0.050 | 0.250 | 1.06 ± 0.06 | 49.77 | 50.23 |
| 55 | 1 | 1 | — | 0.100 | 0.500 | 1.09 ± 0.06 | 51.17 | 48.83 |
| 56 | 1 | 1 | 1 | 0.005 | 0.025 | 0.89 ± 0.35 | 41.78 | 58.22 |
| 57 | 1 | 1 | 1 | 0.010 | 0.050 | 0.65 ± 0.18 | 30.52 | 69.48 |
| 58 | 1 | 1 | 1 | 0.025 | 0.125 | 0.58 ± 0.12 | 27.23 | 72.77 |
| 59 | 1 | 1 | 1 | 0.050 | 0.250 | 0.70 ± 0.16 | 32.86 | 67.14 |
| 60 | 1 | 1 | 1 | 0.100 | 0.500 | 0.38 ± 0.10 | 17.84 | 82.16 |
| 61 | 1 | 1 | 2 | 0.005 | 0.025 | 0.46 ± 0.11 | 21.60 | 78.40 |
| 62 | 1 | 1 | 2 | 0.010 | 0.050 | 0.57 ± 0.19 | 26.76 | 73.24 |
| 63 | 1 | 1 | 2 | 0.025 | 0.125 | 0.51 ± 0.11 | 23.94 | 76.06 |
| 64 | 1 | 1 | 2 | 0.050 | 0.250 | 0.40 ± 0.10 | 18.78 | 81.22 |

TABLE 9-continued

| | Composition contents (Weight ratio) | | | Chitosan Concentration | Amount of chitosan per ton of seeds | Disease development | | Biological effect |
|---|---|---|---|---|---|---|---|---|
| | | | | | | In grade | To control | |
| Ex. | Chitosan | Succinic acid | Glutamic acid | (%) | (kg) | (4 stages) | (%) | (%) |
| 65 | 1 | 1 | 2 | 0.100 | 0.500 | 0.21 ± 0.08 | 9.86 | 90.14 |
| 66 | The amount of Baitan y = 2 kg/t | | | | | 0.33 ± 0.09 | 15.49 | 84.51 |

Note: In the experiments, chitosan having a molecular weight of 800000 D and a degree of deacetylation of 75% was used. For comparison, a pesticide Baitan y (II) widely used for seed treatment was used in Example 20.

Examples 67–71

Examples 67–71 show the effect the composition of the present invention has on Phytophthora of potatoes. Examples 67–71 was conducted under the conditions comparable with one another. All the data are shown in Table 10. The experiment was conducted for the cut leaves of potatoes (cultivar Detskoselskij), which were artificially infected with Phytophthora infestans [Mont.] de Bary. The leaves on the upper part of the potato during the budding to early flowering period were placed into the wet chamber, to which the solution of the composition was sprayed. Immediately after the drying of the drips, the suspension of 3–4 $\mu$l of P. infestans conidia (500,000 conidia/ml) was inoculated on the leaves. On day 3 and 5 after inoculation, the state of the disease state was recorded (5-stage scoring). On the control leaves was sprayed water.

under the condition tested. In these cases, the compositions were used for treatment of the rhizome prior to planting. The method of treatment is the semi-dry method. The criteria for the amount used of the composition was 0.1 kg/t for chitosan and 20 l/t for water. The composition was sprayed on the budding to the early flowering period and 10 days later for a total of two times.

The state of the disease is recorded based on the 5-stage scoring. The number of repetitions of the experiments is 4. The spread of the disease is recorded for the newly harvested rhizome. It was confirmed that the number of healthy rhizomes doubled (relative to the result of the control) when the rhizome was treated prior to planting with the composition of the present invention. Similar results were obtained in the experiment for 3 years.

We are the first to discover that the chitosan-based composition can have a strong biological effect against Phyto-

TABLE 10

| | Composition contents (% by weight) | | | Chitosan Concentration | Disease development | | | |
|---|---|---|---|---|---|---|---|---|
| | | | | | After 3 days | | After 5 days | |
| | | | | | Attach severity | To control | Attach severity | To control |
| Example | Chitosan | Succinic acid | Glutamic acid | (%) | (%) | (%) | (%) | (%) |
| 67 | Comparative example — water | | | — | 1.3 ± 0.10 | 100 | 2.3 ± 0.1 | 100 |
| 68 | 5 | 3 | 2 | 0.004 | 1.1 ± 0.04 | 84.6 | 2.1 ± 0.1 | 91.3 |
| 69 | 5 | 3 | 2 | 0.020 | 1.0 ± 0.06 | 76.9 | 1.5 ± 0.2 | 65.2 |
| 70 | 5 | 3 | 2 | 0.100 | 0.7 ± 0.05 | 53.8 | 1.4 ± 0.1 | 60.9 |
| 71 | 5 | 3 | 2 | 0.500 | 0.05 ± 0.03 | 3.8 | 0.4 ± 0.1 | 17.4 |

Note: In the experiments, chitosan having a molecular weight of 150000 D and a degree of deacetylation of 85% was used.

Examples 72–74

Examples 72–74 were conducted under conditions comparable with one another. The data are shown in Table 11. These examples investigate the effects the composition of the present invention has on the Phytophthora of potatoes phthora. Since Phythophthora is one of the most dangerous injuries to potatoes (and other crops that are produced in large amounts and are required to be stored for a prolonged period of time), these results are not obvious, and are promising. Every year, up to 50% of the potatoes harvested are discarded because of Phythophthora.

TABLE 11

| | Chitosan | | Composition contents (% by weight) | | | Disease development | | | |
|---|---|---|---|---|---|---|---|---|---|
| | Amount | Conc. | | | | Sep. 14, 1975 | | Sep. 21, 1995 | |
| | | | | | | Attach | | Attach | |
| Example | kg/t | (%) | Chitosan | Succinic acid | Glutamic acid | severity | (%) | severity | (%) |
| 72 | Com. Ex. - water | | — | — | — | 1.0 ± 0.1 | 100.0 | 2.3 ± 0.2 | 100.0 |
| 73 | 0.1 | 0.1 | 5 | 3 | 2 | 0.9 ± 0.1 | 90.0 | 1.8 ± 0.2 | 78.0 |

TABLE 11-continued

| | Chitosan | | Composition contents | | | Disease development | | | |
| | | | (% by weight) | | | Sep. 14, 1975 | | Sep. 21, 1995 | |
| | Amount | Conc. | | | | Attach | | Attach | |
| Example | kg/t | (%) | Chitosan | Succinic acid | Glutamic acid | severity | (%) | severity | (%) |
| --- | --- | --- | --- | --- | --- | --- | --- | --- | --- |
| 74 | 0.1 | 0.1 | 5 | 3 | 2 | 0.5 ± 0.1 | 50.0 | 1.4 ± 0.1 | 60.9 |

Note: In the experiments, chitosan having a molecular weight of 150000 D and a degree of deacetylation of 85% was used.

Examples 75–79

Examples 75–79 support the effect of the composition containing chitosan, lactic acid, and the additional ingredients (arachidonic acid derivatives).

This effect has been investigated for the Phythophthora pathogen of potato, *Phythophthora infestans* [Mont.] de Bary. These examples were conducted under conditions comparable with one another. That is, to the slice of potatoes (Gatchinsky sp.) 5 hours after the application of the composition, a suspension of the pathogen's conidia (200,000 conidia/ml) was artificially infected (inoculated). After 5 days, the state of the disease was recorded by the 5-stage scoring. All the data are shown in Table 12.

the five foliage leaf period. After 48 hours, the pathogen was inoculated. The state of the disease of powdery mildew was recorded by the standard method ("Methodological Instructions on the National Testing on Pesticides, Antibiotics and Disinfectants of Crop Seeds," Moscow, 1985, page 130), and that of Phythophthora was recorded by the method of counting the number of conidia after washing the cut leaves. These examples are shown in Table 13.

TABLE 12

| | Composition contents | | | | Disease development | |
| | | | | Additional | (5 days after seeding) | |
| Example | Concentration (%) | Chitosan | Lactic acid (Part by weight) | ingredients | Attach severity | To control (%) |
| --- | --- | --- | --- | --- | --- | --- |
| 75 | Comparative example - water | | | — | 4.4 | 100.0 |
| 76 | 0.1 | 1 | 1 | — | 0.5 | 11.4 |
| 77 | 0.5 | 1 | 1 | — | 0 | 0 |
| 78 | — | — | — | 0.1 | 1.8 | 40.9 |
| 79 | 0.1 | 1 | 1 | 0.1 | 0.14 | 3.2 |

Note: In the experiments, chitosan having a molecular weight of 41600 D and a degree of deacetylation of 75% was used.

Examples 80–81

Examples 80–81 show the effect of the composition on *Oidium erysiphoides* of tomato and *Phythophthora infestans* [Mont.] de Bary. These examples were conducted under the conditions comparable with one another. The Phythophthora-preventing composition was added to the second foliage leaf period of tomato (cultivar Grezanda) and the powdery mildew-preventing composition was added to

TABLE 13

| | Composition contents | | | Severity of attach with powery mildew | | No. of conidia of Phythophthora in 10 discs by microscope | |
| Example | Concentration (%) | Chitosan | Lactic acid (Part by weight) | Disease development (%) | To control (%) | pcs./ml | To control (%) |
| --- | --- | --- | --- | --- | --- | --- | --- |
| 80 | Comparative example - water- | | | 85.9 ± 2.9 | 100 | 26.0 ± 0.7 | 100.0 |
| 81 | 0.1 | 1 | 1 | 22.9 ± 4.4 | 26.7 | 7.0 ± 1.0 | 26.9 |

Note: In the experiments, chitosan having a molecular weight of 125000 D and a degree of deacetylation of 85% was used.

Examples 82–90

Examples 82–90 indicate that the composition can have an effect on the treatment of barley for the purpose of preventing various diseases by a variety of methods, that is, seed treatment, the total treatment of the seeds and during growth, and treatment during growth. In Examples 82–94, the spring barley (cultivar Abava) was cultivated at the experimental farm of a limited company "Tver Seed Company" (Tver oblast) which is a light loam podzol sod drained by conduit under the same field test conditions in the background of a natural high-level infection. The size of the experimental farm is 30 square meters×3. The recording and analysis of the plant pathological evaluation of the tissues harvested was conducted based on the commonly used method ("Methodological Instructions on the National Testing on Pesticides, Antibiotics and Disinfectants of Crop Seeds," Moscow, 1985, page 130).

The data in Examples 82–94 are shown in Table 14, 15, and 16, which can be compared with one another.

Table 14 show the data obtained when the composition of the present invention was used for treatment of the seeds before seeding.

Table 15 show the result of the total treatment of barley including not only the seed treatment before seeding but also the two treatments during the thick-growing and the earring period.

Table 16 show the result of only two sprayings on barley during the thick-growing period and the earring period.

The red stele in Examples 82–94 are caused by *Helminthosporium sativum* Pamm. King et Bakke and Fusaium sp., and the Helminthosporium blotches of the leaves is caused by *Helminthosporium sativum* Pamm. King et Bakke and Drechslera teres Ito.

TABLE 14

| | Composition contents (Part by weight) | | | Amount of ingredient pre 1000 seeds (kg) | | | |
|---|---|---|---|---|---|---|---|
| Example | Chitosan | Succinic acid | Glutamic acid | Chitosan | Heteroauxin | Fluoroxane | FF806 |
| 82 | Control without treatment | | | 0.1 | | | |
| 83 | 5 | 3 | 2 | 0.1 | — | — | — |
| 84 | 5 | 3 | 2 | 0.1 | 0.002 | — | — |
| 85 | 5 | 3 | 2 | 0.1 | 0.002 | 0.002 | — |
| 86 | 5 | 3 | 2 | 0.1 | — | — | 0.005 |

| | Infection of red stele (%) | | | Decreasing of disease sevearity (%) to control at stages: | | |
|---|---|---|---|---|---|---|
| Example | Side shooting | Milky-wax ripeness | Lipening | Side shooting | Milky-wax ripeness | Lipening |
| 82 | 6.2 | 25.0 | 38.3 | — | — | — |
| 83 | 4.1 | 19.6 | 34.1 | 33.9 | 21.6 | 11.0 |
| 84 | 2.7 | 18.1 | 29.2 | 56.4 | 27.6 | 23.8 |
| 85 | 2.0 | 18.1 | 28.4 | 67.7 | 28.0 | 25.8 |
| 86 | 1.9 | 17.1 | 27.9 | 69.3 | 31.6 | 27.1 |

| | Development of Helminthosporium leaf spots % in phase of: | | Attach decrease (%) in phase of: | |
|---|---|---|---|---|
| Example | Side shooting | Ear formation | Side shooting | Ear formation |
| 82 | 8.5 | 25.0 | — | — |
| 83 | Single | 18.0 | 88.2 | 28.0 |
| 84 | Single | 16.9 | 88.2 | 32.4 |
| 85 | Single | 15.0 | 88.2 | 40.0 |
| 86 | Single | 16.0 | 88.2 | 36.0 |

| | Yield structure | | | | | |
|---|---|---|---|---|---|---|
| Example | Number of stems (Stems/sq. meter) | Height of plant (cm) | Length of ear (cm) | No. of seeds/ear (pieces) | Weight of 1,000 grains (g) | Biological yield (t/ha) |
| 82 | 472.3 | 84.2 | 7.1 | 18.0 | 38.1 | 3.24 |
| 83 | 478.3 | 85.1 | 7.2 | 18.4 | 40.0 | 3.52 |
| 84 | 486.0 | 87.4 | 7.3 | 18.0 | 41.0 | 3.59 |
| 85 | 481.3 | 88.5 | 7.2 | 18.2 | 41.2 | 3.59 |
| 86 | 485.3 | 87.9 | 7.3 | 18.0 | 41.0 | 3.58 |

Note: In the experiments, chitosan having a molecular weight of 150000 D and a deacetylation degree of 85% were used.

TABLE 15

| | Composition contents (Part by weight) | | | Amount of ingredient (kg/seed ton, spray concentration) | | | | | | | |
|---|---|---|---|---|---|---|---|---|---|---|---|
| | | | | Chitosan | | Heteroauxin | | Fluoroxane | | FF806 | |
| Example | Chitosan | Succinic acid | Glutamic acid | (kg/t) | (%) | (kg/t) | (%) | (kg/t) | (%) | (kg/t) | (%) |
| 82 | Control (without treatment) | | | | | | | | | | |
| 87 | 5 | 3 | 2 | 0.1 | 0.05 | — | — | — | — | — | — |
| 88 | 5 | 3 | 2 | 0.1 | 0.05 | 0.002 | 0.05 | — | — | — | — |

TABLE 15-continued

| | | | | | | | | | | | |
|---|---|---|---|---|---|---|---|---|---|---|---|
| 89 | 5 | 3 | 2 | 0.1 | 0.05 | 0.002 | 0.05 | 0.0002 | 0.015 | — | — |
| 90 | 5 | 3 | 2 | 0.1 | 0.05 | — | — | — | — | 0.005 | 0.05 |

| | Infection of red stele (%) | | | Decreasing of disease sevearity (%) to control at stages: | | |
|---|---|---|---|---|---|---|
| Example | Side shooting | Milky-wax ripeness | Lipening | Side shooting | Milky-wax ripeness | Lipening |
| 82 | 6.2 | 25.0 | 38.3 | — | — | — |
| 87 | 3.7 | 18.9 | 30.2 | 40.3 | 24.4 | 21.1 |
| 88 | 2.1 | 16.0 | 27.5 | 66.1 | 36.0 | 28.2 |
| 89 | 1.8 | 16.6 | 26.7 | 71.0 | 33.6 | 30.3 |
| 90 | 2.0 | 16.1 | 26.7 | 67.7 | 35.6 | 30.3 |

| | Helminthosporium leaf blight extension (%) at stages: | | Decreasing of disease sevearity (%) to control at stages: | |
|---|---|---|---|---|
| Example | Side shooting (%) | Earring period (%) | Side shooting (%) | Earring period (%) |
| 82 | 8.5 | 25.0 | | |
| 87 | Single | 13.2 | 88.2 | 47.2 |
| 88 | Single | 11.0 | 88.2 | 56.0 |
| 89 | Single | 11.4 | 88.2 | 54.4 |
| 90 | Single | 12.1 | 88.2 | 51.6 |

| | Yield structure | | | | | |
|---|---|---|---|---|---|---|
| Example | Number of stems (Stems/sq. meter) | Height of plant (cm) | Length of ear (cm) | No. of seeds/ear (pieces) | Weight of 1,000 grains (g) | Biological yield (t/ha) |
| 82 | 472.3 | 84.2 | 7.1 | 18.0 | 38.1 | 3.24 |
| 87 | 481.0 | 87.7 | 7.3 | 18.1 | 41.1 | 3.58 |
| 88 | 490.0 | 89.2 | 7.3 | 17.9 | 41.1 | 3.60 |
| 89 | 485.6 | 89.9 | 7.3 | 17.9 | 41.5 | 3.61 |
| 90 | 490.0 | 89.0 | 7.3 | 17.9 | 41.1 | 3.60 |

Note: In the experiments, chitosan having a molecular weight of 150000 D and a deacetylation degree of 85% were used.

TABLE 16

| | Composition contents (Part by weight) | | | Amount of ingredient (spray concentration) | | | |
|---|---|---|---|---|---|---|---|
| Example | Chitosan | Succinic acid | Glutamic acid | Chitosan (%) | Heteroauxin (%) | Fluoroxane kg/ha | FF806 (%) |
| 82 | Control without treatment | | | — | — | — | — |
| 91 | 5 | 3 | 2 | 0.05 | — | — | — |
| 92 | 5 | 3 | 2 | 0.05 | 0.05 | — | — |
| 93 | 5 | 3 | 2 | 0.05 | 0.05 | 0.015 | — |
| 94 | 5 | 3 | 2 | 0.05 | — | — | 0.05 |

| | Root rot (%) developed in phase of: | | Attach decrease (%) in phase of: | | Helminthosporium leaf spots | |
|---|---|---|---|---|---|---|
| Example | Milky-wax ripeness (%) | Lipening (%) | Milky-wax ripeness (%) | Lipening (%) | Development in phase of ears-formation (%) | Attach decrease (%) to control |
| 82 | 25.0 | 38.3 | | | 25.0 | |
| 91 | 22.0 | 31.7 | 12.0 | 17.2 | 18.1 | 27.6 |
| 92 | 20.1 | 30.8 | 19.6 | 19.6 | 17.6 | 29.6 |
| 93 | 19.3 | 31.2 | 22.8 | 18.5 | 15.0 | 40.0 |
| 94 | 20.2 | 29.1 | 19.2 | 24.0 | 15.8 | 36.8 |

| | Yield structure | | | | | |
|---|---|---|---|---|---|---|
| Example | Number of products (Stems/sq. meter) | Height of plant (cm) | Length of ear (cm) | No. of seeds/ear (pieces) | Weight of 1,000 grains (g) | Biological yield (t/ha) |
| 82 | 472.3 | 84.2 | 7.1 | 18.0 | 38.1 | 3.24 |
| 91 | 460.0 | 85.4 | 7.0 | 18.2 | 41.5 | 3.47 |
| 92 | 477.0 | 86.0 | 7.1 | 18.2 | 40.1 | 3.48 |
| 93 | 478.0 | 86.8 | 7.2 | 18.2 | 40.9 | 3.56 |
| 94 | 470.6 | 85.3 | 7.2 | 18.1 | 41.2 | 3.51 |

Note: In Table 17, chitosan having a molecular weight of 150000 D and a deacetylation degree of 85% was used.

Examples 95–97

Examples 95–97 indicate that the composition of the present invention having various compositions can have good effects even under the industrial conditions of treatment (seed treatment, total treatment of the seeds and during growth, and treatment during growth) by various methods for the purpose of preventing various diseases. In this case, barley (cultivar Abava) was cultivated at the experimental farm of a limited company "Tver Seed Company" under the field condition of the industrial experiment. This was conducted at the experimental farm of a light loam podzol sod and which was equipped with the conduit drainage system in the natural high infection background. The size of the experimental farm is 0.5 hectare×3. The plant pathological recording and analysis of the tissues of the harvest were conducted based on the commonly used method ("Methodological Instructions on the National Testing on Pesticides, Antibiotics and Disinfectants of Crop Seeds," Moscow, 1985, page 130).

Red stele in Examples 95–97 was caused by *Helminthosporium sativum* Pamm. King et Bakke and Fusarium Sp., and Helminthosporium blotches of the leaves was caused by Drechslera teres Ito (meshed blotch), *Helminthosporium sativum* Pamm. King et Bakke (dark brown blotch), and Drechslera teres Ito (muscular blotch). The seeds were treated 7 days before seeding using the disinfection machine IIC-5 at an amount of 0.1 kg/t (in terms of chitosan in the composition). Spraying onto barley during growth was conducted once with the composition having a chitosan concentration of 0.05% using the OII-2000 type tractor sprayer at the time of earring. All the data in Examples 95–97 are shown in Table 17.

Examples 98–101

Examples 98–101 indicate that the composition having the composition of the present invention can have an effect on the harvesting of carrots and the prevention of damping-off when used for the treatment of the seeds of carrots before seeding. As the control experiment, the traditional treatment with 6 g/kg tetramethylthiuram disulfide was conducted. The carrots were cultivated under the field test condition. After harvesting, the state of damping-off (Fusarium sp.) was investigated for the roots (inoculated under the condition of the wet chamber). Examples 98–101 are derived from the experiments under the conditions comparable with one another and all the data are shown in Table 18.

TABLE 17

| | Composition contents (part by weight) | | | Root rot development in phase of milky-wax ripeness | |
|---|---|---|---|---|---|
| Example | Chitosan | Succinic acid | Glutamic acid | Development (%) | Attach decrease (%) to control |
| 95 | Control without treatment | | | 65.0 | — |
| 96 | 5 | 4 | 1 | 45.3 | 30.3 |
| 97 | 5 | 4 | 1 | 35.4 | 45.5 |

| | Development of Helminthosporium leaf spots in milky-wax ripening | | | | | |
|---|---|---|---|---|---|---|
| | *Drechslera teres* | | *H. sativum* | | *Drechslera graminea* | |
| Example | Development (%) | Decrease of severity (%) | Development (%) | Decrease of severity (%) | Development (%) | Decrease of severity (%) |
| 95 | 42.0 | | 32.4 | | 24.3 | |
| 96 | 35.6 | 15.2 | 29.3 | 9.6 | 20.0 | 17.7 |
| 97 | 28.2 | 32.8 | 20.7 | 36.1 | 16.4 | 32.1 |

| | Yield structure | | | | | |
|---|---|---|---|---|---|---|
| Example | Number of products (Stems/sq. meter) | Height of plant (cm) | Length of ear (cm) | No. of seeds/ear (pieces) | Weight of 1,000 grains (g) | Biological yield (t/ha) |
| 95 | 425.6 | 54.0 | 6.0 | 17.6 | 46.4 | 3.48 |
| 96 | 428.4 | 52.8 | 6.0 | 17.4 | 50.0 | 3.78 |
| 97 | 439.6 | 54.1 | 6.0 | 17.7 | 49.5 | 3.85 |

Note: In the experiment, chitosan having a molecular weight of 300000 D and a deacetylation degree of 90% was used.

TABLE 18

| Ex. | Chitosan | Succinic acid | Glutamic acid | Fluoroxane rate (kg/t) | Yield per unit area (t/ha) | (%) | Stems of root-plants infected with Fusarium |
|---|---|---|---|---|---|---|---|
| 98 | Control (treated with 6 g/kg tetramethyl thiuraum) | | | | 33.0 | 100 | 42 |
| 99 | 5 | 3 | 2 | — | 38.0 | 115 | 8 |
| 100 | 5 | 3 | 2 | 0.00005 | 41.2 | 125 | 20 |
| 101 | 5 | 3 | 2 | 0.0002 | 43.0 | 130 | 12 |

Note: In the examples of Table 18, chitosan having a molecular weight of 800000 D and a deacetylation degree of 82% was used, which was immersed in the composition containing 0.2% chitosan, or 2 kg of the agent in 1 ton of the seeds. The experiment was conducted using the standard disinfection machine at the acceptable limit of tetramethyl thiuram concentratino in the air in the used zone of 0.5 mg/cubic meter at an amount of 6 g of the seeds/kg.

What is claimed is:

1. A composition for enhancing resistance to plant diseases comprising the following ingredients:
   (1) 0.004–0.500% by weight of a chitosan with a molecular weight of 800–150,000 and a degree of deacetylation of 65–97%;
   (2) 0.004–0.500% by weight of one or more organic acids selected from the group consisting of lactic acid, succinic acid and glutamic acid or a salt thereof;
   (3) one to three biologically active substances selected from the group consisting of a natural or synthetic plant hormone, a natural unsaturated fatty acid or synthetic derivative thereof, an alkyldimethylbenzyl ammonium salt of a copolymer of N-vinyl pyrrolidone and crotonic acid, phenolic acid, and an inorganic acid; and
   (4) water as remainder;
   wherein the weight ratio of (1) to (2) is 1:1 and the weight ratio of (3) to (1) is 0.0002–2:1; and
   the pH of the composition is 5.6–6.0.

2. The composition according to claim 1 wherein said plant hormone is heteroauxin or a synthetic fluorine compound.

3. The composition according to claim 1 wherein the natural unsaturated fatty acid or a synthetic derivative thereof in said ingredient (3) is oleic acid, linoleic acid, linolenic acid, arachidonic acid or 12-oxy-cis-9-octadecenic acid methyl ether.

4. The composition according to claim 1 wherein the phenolic acid in said ingredient (3) is salicylic acid.

5. The composition according to claim 1 wherein the inorganic acid in said ingredient (3) is monosodium phosphite.

6. A composition for enhancing resistance to plant diseases comprising the following ingredients:
   (1) 0.004–0.500% by weight of a chitosan with a molecular weight of 41,600–800,000 and a degree of deacylation of 75–90%;
   (2) 0.004–0.500% by weight of one or more organic acids selected from the group consisting of lactic acid, succinic acid and glutamic acid or a salt thereof;
   (3) water as remainder;
   wherein the weight ratio of (1) to (2) is 1:1; and
   the pH of the composition is 5.6–6.0.

7. The composition according to claim 6, said composition further comprising, in addition to the above ingredients, a biologically active substance which is a natural or a synthetic plant hormone, or a natural unsaturated fatty acid or a synthetic derivative thereof at a ratio of 0.002–0.2 part by weight per one part by weight of chitosan.

8. The composition according to claim 7 wherein said natural or synthetic plant hormone is heteroauxin, an ethyl ether hydrochloride of fluoroxane($\alpha$-(4-methylaminobenzene)-$\beta$, $\beta$, $\beta$-lactate trifluoride, or a synthetic fluorine compound.

9. The composition according to claim 7 wherein said natural unsaturated fatty acid or a synthetic derivative thereof is the methyl ether of arachidonic acid, or 12-oxy-cis-9-octadecenic acid.

10. A method of increasing resistance to diseases in plants comprising administering to said plant an effective amount of a composition according to any one of of claim 1 or 6.

11. A composition for enhancing resistance to plant diseases comprising the following ingredients:
   (1) 0.004–0.500% by weight of a chitosan with a molecular weight of 800–150,000 and a degree of deacetylation of 65–97%;
   (2) 0.004–0.500% by weight of succinic acid;
   (3) a member from the group consisting of oleic acid, linoleic acid, arachodonic acid, 12-oxy-cis-9-octadecenic acid methyl ester, salicylic acid and monosodium phosphite;
   (4) water as remainder;
   wherein the weight ratio of (1) to (2) is 1:1 and the weight ratio of (3) to (1) is 0.0002–2:1; and
   the pH of the composition is 5.6–6.0.

12. A method of increasing resistance to diseases in plants comprising administering to said plant an effective amount of a composition according to claim 11.

* * * * *